United States Patent
Marlin

(12) 
(10) Patent No.: US 6,426,429 B1
(45) Date of Patent: Jul. 30, 2002

(54) PROCESS FOR THE PREPARATION OF HINDERED PHOSPHITES

(75) Inventor: Gary Vincent Marlin, Morgantown, WV (US)

(73) Assignee: General Electric Company, Pittsfield, MA (US)

( * ) Notice: Subject to any disclaimer, the term of this patent is extended or adjusted under 35 U.S.C. 154(b) by 13 days.

(21) Appl. No.: 09/636,776

(22) Filed: Aug. 11, 2000

(51) Int. Cl.$^7$ ............................................. C07F 9/6574
(52) U.S. Cl. ........................................... 558/78; 558/85
(58) Field of Search ..................... 558/78, 85

(56) References Cited

U.S. PATENT DOCUMENTS

| | | | |
|---|---|---|---|
| 3,281,506 A | 10/1966 | Shepard et al. ............... | 558/96 |
| 4,116,926 A | 9/1978 | York .......................... | 524/120 |
| 4,237,075 A | 12/1980 | Gough ........................ | 558/96 |
| 4,290,976 A | 9/1981 | Hechenbleikner et al. .... | 558/78 |
| 4,312,818 A | 1/1982 | Maul et al. .................... | 558/96 |
| 4,356,129 A | 10/1982 | Hucks et al. ................ | 260/973 |
| 4,371,647 A | 2/1983 | Minagawa et al. ......... | 524/120 |
| 4,440,696 A | 4/1984 | Maul et al. ................... | 558/96 |
| 4,492,661 A | 1/1985 | Maul et al. ................... | 558/96 |
| 4,656,302 A | 4/1987 | Dressler ..................... | 558/194 |
| 4,705,879 A | 11/1987 | Dressler ..................... | 558/194 |
| 4,739,090 A | 4/1988 | Tajima et al. ................. | 558/78 |
| 4,894,481 A | 1/1990 | Burt ............................ | 568/12 |
| 5,103,035 A | 4/1992 | Elnagar et al. ............... | 558/96 |
| 5,126,475 A | 6/1992 | Bahrmann et al. ............ | 558/85 |
| 5,141,975 A | 8/1992 | Enlow ........................ | 524/128 |
| 5,247,118 A * | 9/1993 | Blosser et al. ............... | 558/118 |
| 5,308,901 A * | 5/1994 | Hobbs et al. ................ | 524/120 |
| 5,438,086 A | 8/1995 | Stevenson et al. .......... | 524/120 |
| 5,919,966 A | 7/1999 | Marlin ........................ | 558/78 |

FOREIGN PATENT DOCUMENTS

| | | |
|---|---|---|
| EP | 356688 | 3/1990 |
| JP | 05059074 | 3/1993 |

OTHER PUBLICATIONS

Foreign Search Report Oct. 18, 2001.

* cited by examiner

Primary Examiner—Fiona T. Powers

(57) ABSTRACT

A process to produce organic phosphites from the group consisting of:

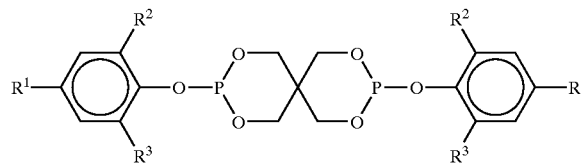

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl; and

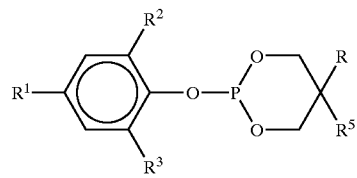

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl and each $R^4$ and $R^5$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl using a metal phenolate

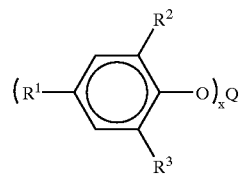

where each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl, and Q is a metal cation having a valence x, i.e. oxidation state, to drive the reaction to completion.

20 Claims, No Drawings

PROCESS FOR THE PREPARATION OF HINDERED PHOSPHITES

FIELD OF THE INVENTION

This invention relates to a process for the preparation of organic phosphites, specifically hindered phosphites.

BACKGROUND OF THE INVENTION

Organic phosphites are used in the stabilization of a wide variety of polymeric systems. Many different phosphites have been proposed for use either alone or in combination with other stabilizers. Such phosphites and their utilities are described in U.S. Pat. Nos. 4,371,647, 4,656,302, 4,705;879, 5,126,475, 5,141,975, and 5,438,086. The importance of organic phosphites as stabilizers has lead to the development of a variety of specialty organic phosphites that have enhanced effectiveness for stabilization.

Sterically hindered organic phosphites, and in particular phosphates based upon glycols or polyhydric alcohols (e.g. pentaerythritol) and containing alkyl, aryl, or alkyl-substituted aryl groups wherein the substitution is selected from the group consisting of t-butyl, t-amyl, t-hexyl, cyclohexyl, t-pentyl, and t-octyl, are especially desirable compounds due to their enhanced hydrolytic stability, ease of handling and compatibility with a wide variety of polymeric systems. The phosphite esters prepared from sterically hindered alcohols are also especially preferred for their improved hydrolytic stability over other alkyl substituted phosphites as well as their enhanced compatibility with some polymeric resins, especially polyolefins.

The organic diphosphites are generally prepared using methods involving reactions between the appropriate hydroxy compounds and phosphorous trihalides, e.g., phosphorous trichioride. Such methods and other useful methods are described in U.S. Pat. Nos. 3,839,506, 4,116,926, 4,290, 976, 4,440,696, and 4,492,661. The ease of substitution of the halides on the phosphorous trihalide decreases as each halide is replaced. For example, in the preparation of bis(aryl)pentaerithritol diphosphites, the pentaerithritol hydroxyls readily react with a phosphorous trihalide to yield a bis(disubstituted halo phosphite (i.e., an intermediate di-substituted diphosphorohalidite). The displacement of the third halo group is less than quantitative and is considerably slower in rate. Additionally, displacement of the third halo group by a sterically hindered phenol is even more difficult and requires elevated temperatures and/or use of a catalyst.

In order to increase the rate of reaction and the degree of completion for displacing the third halide with a sterically hindered moiety, various techniques have been generally utilized in the art. These techniques include: elevating the reaction mixture temperature and the use of hydrogen halide acceptors, e.g., amines. Such techniques are described in U.S. Pat. Nos. 3,281,506, 4,237,075, 4,312,818, 4,440,696, and 4,894,481.

Generally in the case of diphosphites derived from sterically hinderd alcohols, the procedures of the prior art result in undesirable product mixtures. Additionally, various by-product phosphite compounds are also formed leading to low yields of the desired product. The resulting phosphite mixture containing a halo-phosphite is extremely difficult to purify and the residual halo-phosphite can lead to acid impurities that affect the long term stability of the desired organic phosphite, as well as affecting the stability of thermoplastic compositoins where the phosphite is employed as a stabilizer.

Various processes have been described in the prior art yet each suffers from some undesirable limitation. For example, U.S. Pat. No. 4,739,090 describes a process utilizing xylene as a solvent. The final product is isolated by filtration and the filtrate can be recycled. This process is deficient in resulting in at least about five percent or more impurities that require further crystallization to remove. This patent is silent on the form of the pentaerythritol utilized in the reaction.

U.S. Pat. No. 5,103,035 describes low temperature reaction conditions in chlorinated solvents. This process is undesirable due the difficulties in safely handling chlorinated solvents and a second solvent has to be utilized in order to bring the final product out of solution.

U.S. Pat. No. 5,438,086 describes a process for making diphosphites based upon pentaerythritol and 2,4-dicumylphenol wherein the dicumyl phenol is first reacted with phosphorous trichloride followed by allowing the reaction with the pentaerythritol. This process afforded only a 66% yield and acid numbers of 2 to 6, both of which are unacceptable.

It is therefore apparent that a need continues to exist for improved processes for the preparation of phosphite esters prepared from sterically hindered alcohols.

SUMMARY OF THE INVENTION

The present invention provides for a process to produce organic phosphites from the group consisting of:

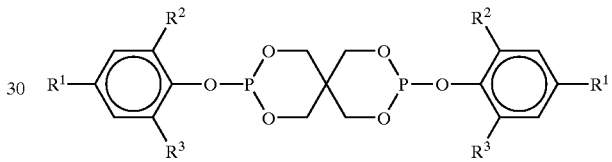

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl; and

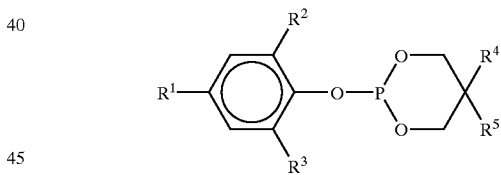

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl and each $R^4$ and $R^5$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl comprising:

(a) a first step comprising reacting a glycol selected from the group consisting of pentaerythritol and

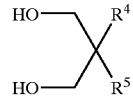

where $R^4$ and $R^5$ are independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with a phosphorus tri-halide to produce a first product comprising a halo phosphite ester of the glycol;

(b) reacting the first product with a phenol having the formula:

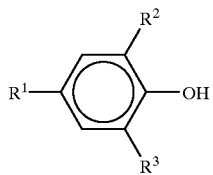

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl to produce a second product comprising the organic phosphite and the halo phosphite; and (c) reacting the second product with a metal phenolate compound comprising a compound of the formula:

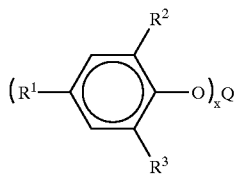

where each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl, and Q is a metal cation having a valence x to produce a third product comprising the organic phosphite and the halo phosphite wherein the halo phosphite is present in an amount below about 2.0 mole percent.

DETAILED DESCRIPTION OF THE INVENTION

The present invention relates to processes to produce organic phosphites from the group consisting of:

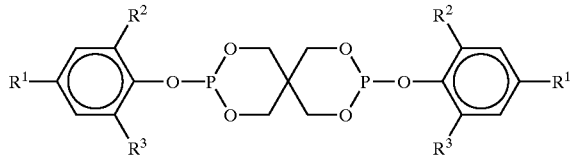

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl; and

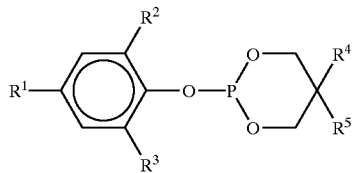

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl and each $R^4$ and $R^5$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

In general, organic phosphites are typically produced by reacting a phosphorous trihalide, e.g., phosphorous trichloride, with hydroxyl-containing compounds wherein the halides are displaced on the phosphorous trihalide by the hydroxyl-containing compounds. The ease of substitution by the hydroxyl-containing compounds depends at least partly on the steric bulk of the hydroxyl-containing compounds. When the hydroxyl-containing compound has a low steric demand (i.e. the hydroxyl-containing compound is not a sterically hindered hydroxyl-containing compound), the displacement of the halides is somewhat statistical. However, as the steric demand of the hydroxyl-containing compound increases, increased selectivity may be obtained to achieve less substituted halophosphites. For reactions involving low steric demand, the displacement of the first two halides on the phosphorous trihalide are generally facile and proceed to completion without the need for catalysis. When there is a, high steric demand, frequently no reaction will occur in the absence of catalysis.

In the displacement of the third halide moiety from the di-substituted phosphorus halide, the degree of conversion to the tri-substituted phosphite is adversely affected by steric considerations of both the di-substituted phosphorus halide and the hydroxyl-containing compound. Catalysts, including amines, are often employed to increase the degree of conversion to the tri-substituted phosphite. Unfortunately, amine catalysts generally result in insoluble amine halide salt impurities in the desired phosphite compound and purification steps must be undertaken to remove the salt.

Elevating the temperature of the reaction mixture is also known to assist in driving the reaction towards completion. In the case of spiro bis-phosphites derived from pentaerythritol, elevating the temperature above about 80° C. leads to increases in the level of byproducts of the general formulas:

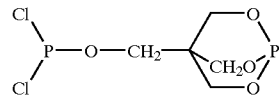

(a halo phosphite specie, e.g. chloro phosphite ester) and

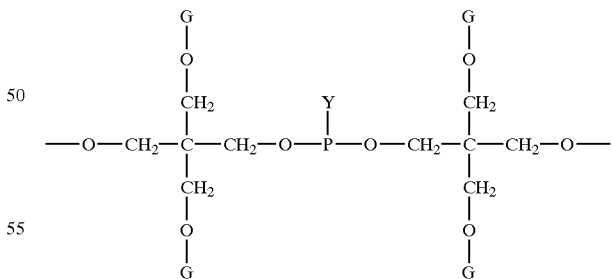

wherein Y is halogen or another good leaving group and each G can independently be a phosphorous or hydrogen increases as the temperature is increased beyond about 80° C. When G is a phosphorous, various polyphosphite compounds are also possible. These byproducts and other similar by-products are difficult to remove from the desired spiro bisphosphite compound and can have a negative affect on the stability of the desired spiro bisphosphite and for these reasons are extremely undesirable.

After the addition of the phosphorous trihalide is competed, the reaction may be driven towards completion by slowly raising the temperature of the reaction mixture to about 90° C. over a long period of time generally ranging from about 3 to about 10 hours. The solvent may be at least partially removed, typically by application of a vacuum, to insure complete removal of the hydrogen halide by-product and to yield the desired product. The degree of completion of the reaction may be followed by standard techniques in this art, including, for example, by liquid or gas chromatography. Typical reaction times to substantial completion are up to about 24 hours. Preferably, the temperature and pressure conditions are selected to afford the maximum mount of product within a time period of about 8 to about 12 hours.

The process of the present invention comprises the step of adding a phenolate compound of the formula:

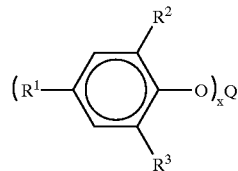

(hereinafter referred to as metal phenolate) where each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl, and Q is a metal cation having a valence x, i.e. oxidation state to the reaction to prepare phosphite esters. The oxidation state or valence (used interchangeably herein) of the metal cation Q may vary in integer values between 1 and 4. Metal phenolate is added to the reaction to prepare phosphite esters of hindered alcohols to drive the reaction to completion by the formation of halide salts of the metal cation Q. Q may be any metal cation that is synthetically convenient, wherein the corresponding phenolate salt may correspond to the phenolate esters used for the preparation of the phosphite esters of hindered alcohols, i.e. organic phosphites from the group consisting of:

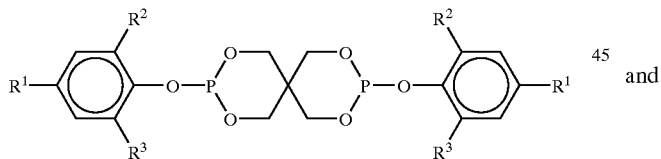

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl; and

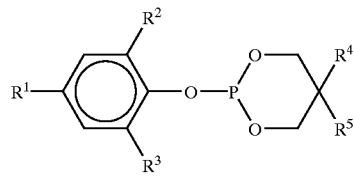

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl and each $R^4$ and $R^5$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl. Preferably $R^1$, $R^2$ and $R^3$ are sterically hindered radicals such as t-butyl, t-amyl, t-hexyl, cyclohexyl, cumyl, t-pentyl, and t-octyl; more preferably $R^1$, $R^2$ and $R^3$ are sterically hindered radicals such as t-butyl, t-amyl, t-hexyl, cyclohexyl, and cumyl; and most preferably $R^1$, $R^2$ and $R^3$ are sterically hindered radicals such as t-butyl, t-amyl, and cyclohexyl.

The metal cations, Q, most suitable for the metal phenolate salt added in the process of the invention are selected from the group consisting of the alkali metals, the alkaline earth metals, the transition metals and the non-transition metals of Groups III, IV and V subject to the limitation that the halides of these metals are ionic salts. By halides the term includes the elements of Group VII of the periodic table, i.e. fluorine, chlorine, bromine, iodine and astatine. Preferred metals are the alkali metals and the alkaline earth metals; more preferred metals are the alkali metals; and the most preferred metals are sodium and potassium.

It may be desirable to use a mixture of phenolate salts, each of which individually satisfies the above recited definition of phenolate compound but which differ in the selection of the metal cation Q or in the choice of the substitutent groups, $R^1$, $R^2$, and $R^3$.

The use of the metal phenolate in conjunction with partially reacted phosphorus tri-halide (halo-phosphite ester) drives the reaction to completion forming an ionic metal halide salt that is either only sparingly soluble in the reaction mixture or insoluble and thus the reaction is driven to completion by metathesis. In using the term "completion" Applicant defines a completed reaction as being one where the quantity of halo-phosphite ester species, i.e fluoro-, chloro-, bromo,or iodo-phosphite ester or any mixture of these, as being below about 2.0 mole percent in the reaction mixture, preferably below about 1.0 mole percent, more preferably below about 0.50 mole percent, and most preferably below about 0.25 mole percent. Specifically the halo phosphite ester is selected from the group consisting of:

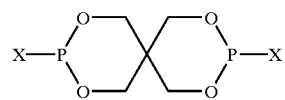

and

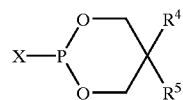

where X is selected from the group of halogens, fluorine, chlorine, bromine and iodine and $R^4$ and $R^5$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl. The phosphite product can also be purified using filtration, melt crystallization techniques or combinations of melt crystallization and solvent crystallization and/or precipitation.

When the phosphite stabilizer is isolated in crystalline form, the present invention contemplates that it may be utilized in solid amorphous form. The amorphous phosphite composition is formed by rapid cooling of melt of the phosphite. Such melt may be a mixture of the phosphite and polyamine which is rapidly cooled to form a solid amorphous phosphite composition. The amorphous nature of composition enhances the hydrolytic stability of the solid composition compared to crystalline composition containing the same constituents.

The phosphites that can be made by the process of the present invention include all organic phosphites derived from glycols and polyhydric alcohols, particularly glycols with phosphorus tri-halide and with hydroxyl-containing compounds of the general formula:

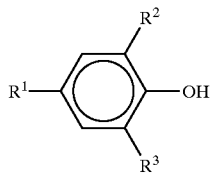

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl. Especially preferred phosphites, however, are sterically hindered Spiro phosphites wherein one of the ester groups of the phosphite is formed from hydroxyl-containing compounds of the general formula:

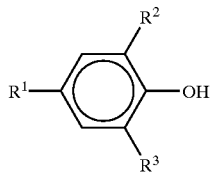

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of RI and $R^2$ is t-butyl, t-amyl, t-hexyl, cyclohexyl, cumyl, t-pentyl, or t-octyl. In the practice of the present invention, a preferred organic spiro phosphite is of the formula:

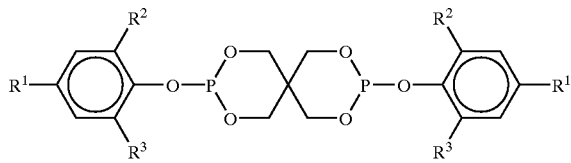

wherein each $R^1$, $R^2$ and $R^3$ is t-butyl. In the practice of the present invention another preferred sterically hindered phosphite is of the formula:

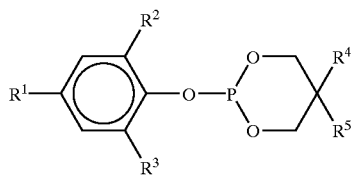

wherein each $R^1$, $R^2$ and $R^3$ is t-butyl, $R^4$ is ethyl and $R^5$ is butyl.

A preferred method of preparing the phosphite ester of the following structural formula:

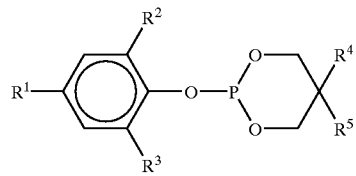

is to select a glycol having the formula:

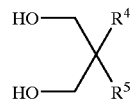

where $R^4$ and $R^5$ are independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl where in this case $R^4$ is butyl and $R^5$ is ethyl (or alternatively pentaerythritol) and in a first step react the selected glycol with a phosphorus tri-halide $PPX_3$, where the halide, X, is halogen as previously defined, specifically phosphorus tri-chloride to produce a a first product the halo-phosphite ester, specifically:

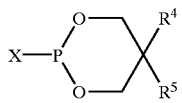

where X is chlorine, $R^4$ is butyl and $R^5$ is ethyl. This is followed by a second step wherein the halo-phosphite ester is reacted with a phenol having the structure:

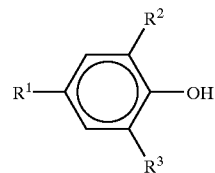

where $R^1$, $R^2$, and $R^3$ are all t-butyl groups. These two steps will normally produce a second product comprising the desired phosphite ester in excess of 97 mole percent yield. However, as previously noted with sterically hindered phosphite esters it is difficult to achieve essentially complete reaction, i.e. to have less than about 2 mole percent of the halo-phosphite ester remaining in the reaction product. A third step is added to the process comprising the first two steps where the second product is further reacted with a metal phenolate salt of the formula:

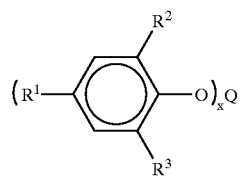

where $R^1$, $R^2$, and $R^3$ are all t-butyl groups, Q is sodium and because the valence or oxidation state of sodium is +1, x is 1, thereby converting the remaining halophosphite to the desired phosphite ester product, the third product, as defined by the choices of the various R groups, phosphorus halide and glycol, having less than about 2 mole percent of the halo-phosphite ester remaining in the third product. This synthesis is particulary convenient because with certain particular choices of the glycol and phenol the desired phosphite ester is soluble in the reaction mixture while the by-product of the reaction of the metal phenolate with unreacted halo-phosphite ester produces a solid, metal halide that is simply and conveniently removed by filtration.

Because mixtures of compounds may produce certain other processing advanatges, it is conceivable that the choice of R groups for the metal phenolate in step 3 might be different from those chosen for the phenol. Completion of the reaction is defined by the mole percent of unreacted halo-phosphite ester remaining, the reaction beiung essentially complete when the quantity of halo-phosphite ester is below about 2.0 mole percent in the reaction mixture, preferably below about 1.0 mole percent, more preferably below about 0.50 mole percent, and most preferably below about 0.25 mole percent. In a particular embodiment, the more complete conversion of the halophosphirte ester to the desired product increases product yield. The increase in product yield may be accomplished by use of an amine solvent and filtering the amine halide and metal halide reaction products from the reaction mixture after removal of the alcohol from the reaction mixture can allow the isolation of a phosphite ester having a fairly high purity. This particular embodiment eliminates several time-consuming and expensive process steps, e.g. crystallization, filtration and drying.

This method may be used to prepare phosphite esters of the formula:

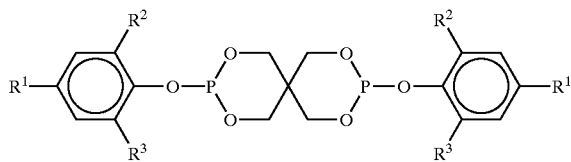

by choosing pentaerythritol as the glycol or polyhydric alcohol to be reacted with the phosphorus tri-halide.

All U.S. patents cited by reference herein are herewith incorporated by reference. In order that those skilled in the art will be better able to practice the invention, the following examples are given by way of illustration and not by way of limitation.

EXAMPLES

The following experiment was based on taking a sample of a reaction mixture from a commercial reactor operated to produce

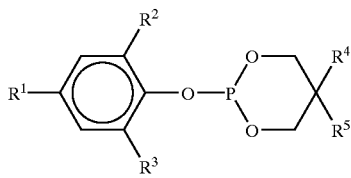

where each $R^1$, $R^2$ and $R^3$ is t-butyl, $R^4$ is ethyl and $R^5$ is butyl, i.e. 2-butyl-2-ethyl-1,3-propanediol-(2, 4, 6-tri-t-butylphenyl) phosphite, using a metal phenolate of the formula:

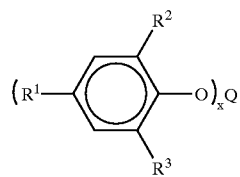

where $R^1$, $R^2$, and $R^3$ are each t-butyl, x is 1 and Q is sodium to drive the reaction to completion. The starting materials were 2-butyl-2-ethyl-1,3-propanediol, phosphorus trichloride and 2, 4, 6-tri-t-butylphenol in tri-propyl amine solvent. The reaction was carried out at 70–75° C. for about 3 hours. After about 3 hours an 86.45 g sample of the reaction mixture was taken from the commercial reaction vessel and warmed to 70–75° C. The sample was analyzed by gas chromatography for the presence of (2-butyl-2-ethyl-propanediol) chlorophosphite and (2-butyl-2-ethylpropanediol) which is the first stage hydrolysis product of (2-butyl-2-ethyl-propanediol) chlorophosphite. A 4.25 g quantity of a slurry of approximately 25 weight percent sodium 2, 4, 6-tri-t-butylphenolate in tripropylamine was added to the sample of the reaction mixture taken from the commercial reactor. The amount of slurry added was based on the following equation:

DETAILED DESCRIPTION OF THE INVENTION

Grams of slurry to add=grams of sample×0.14(%CLPH+ %BEPD Phos)×100/% NaOTTBP (see notes to Table 1 for definitions). The calculated amount of slurry was added to the reaction mixture and the sample was occasionally shaken during a three hour period, holding the sample at a temperature ranging from 70 to 75 ° C. After the three hour period the sample was again analyzed for the presence of (2-butyl-2-ethyl-propanediol) chlorophosphite. Because the reaction had not been driven to completion the previously referenced calculation was repeated. An additional 2.18 g quantity of the slurry of approximately 25 weight percent sodium 2, 4, 6-tri-t-butylphenolate in tripropylamine was added to the sample of the reaction mixture and the mixture allowed to continue to react at a temperature ranging from 70 to 71 ° C. for an additional 95 minutes. The results of analyzing the various samples are presentedf in Table 1.

TABLE 1

Analysis of Addition of sodium 2,4,6-tri-t-butylphenolate to Reaction Mixture to Make 2-butyl-2-ethyl-1,3-propanediol-(2,4,6-tri-t-butylphenyl) phosphite

| Analysis | | After Additional Reaction | |
|---|---|---|---|
| (Weight %) | Initial | First Addition | Second Addition |
| tripropylamine | 40.10 | 41.76 | 42.12 |
| CLPH[1] | 0.83 | 0.33 | 0.01 |
| 2,4,6-TTBP[2] | 12.86 | 12.62 | 12.53 |
| BEPD phos[3] | 0.40 | 0.12 | 0.11 |
| BEPD-TTBP[4] | 44.80 | 44.28 | 44.34 |

1. CLPH is the 2-butyl-2-ethyl-1,3-propanediol chlorophosphite left unreacted in step 2. It is the objective of this process to cause it to react fully, that is disappear from the analysis.
2. 2,4, 6 -tri-t-butyl phenol
3. BEPD phos is a hydrolysis product of CLPH, i.e. 2-butyl-2-ethyl-1,3-propanediol phosphorus acid (the acid ester).

In this analysis, a small amount of water in the analysis solvent converts the chlorophosphite to the acid ester, so some of the "BEPD phosphite" which in the sample is actually CLPH disappears also through reaction with the Na 2,4, 6 -tri-t-butylphenolate (NaOTTBP).

4. 2-butyl-2-ethyl-1,3-propanediol-(2, 4, 6-tri-t-butylphenyl) phosphite

What is claimed:

1. A process to produce organic phosphites from the group consisting of:

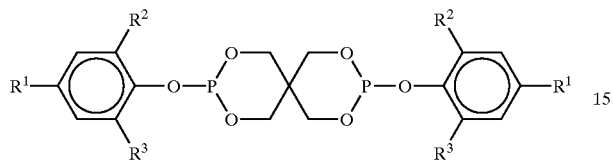

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl; and

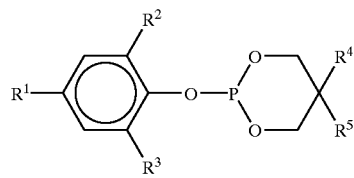

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl and each $R^4$ and $R^5$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl comprising:

(a) a first step comprising reacting a glycol selected from the group consisting of pentaerythritol and

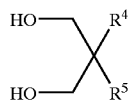

where $R^4$ and $R^5$ are independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with a phosphorus tri-halide to produce a first product comprising a halo phosphite ester of the glycol;

(b) reacting the first product with a phenol having the formula:

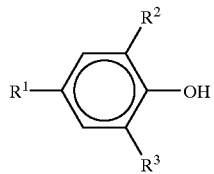

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl to produce a second product comprising the organic phosphite and the halo phosphite; and (c) reacting the second product comprising the organic phosphite and the halo phosphite with a metal phenolate compound comprising a compound of the formula:

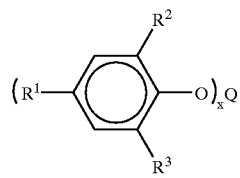

where each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl, and Q is a metal cation having a valence x to produce a third product comprising the organic phosphite and the halo phosphite wherein the halo phosphite is present in an amount below about 2.0 mole percent.

2. The process of claim 1 where the glycol is

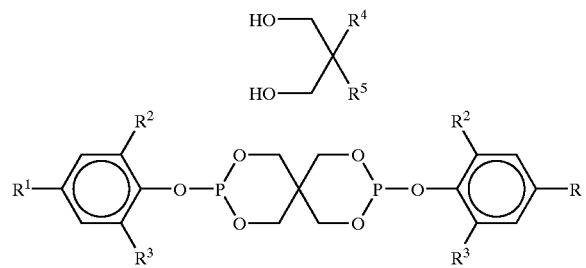

where $R^4$ and $R^5$ are independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

3. The process of claim 2 where the phosphorus tri-halide is phosphorus trichloride.

4. The process of claim 3 where $R^1$, $R^2$ and $R^3$ of the phenol compound

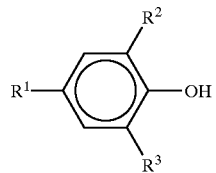

are all t-butyl.

5. The process of claim 4 where $R^1$, $R^2$ and $R^3$ of the phenol compound

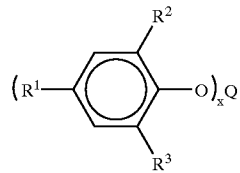

are all t-butyl, Q is sodium and x is 1.

6. The process of claim 5 wherein the halo phosphite is present in an amount below about 1.0 mole percent.

7. The process of claim 5 wherein the halo phosphite is present in an amount below about 0.5 mole percent.

8. The process of claim 5 wherein the halo phosphite is present in an amount below about 0.25 mole percent.

9. The process of claim 6 wherein $R^4$ is butyl and $R^5$ is ethyl for the glycol.

10. The phosphite ester produced by the process of claim 1.

11. The phosphite ester produced by the process of claim 2.

12. The phosphite ester produced by the process of claim 3.

13. The phosphate ester produced by the process of claim 4.

14. The phosphite ester produced by the process of claim 5.

15. The phosphate ester produced by the process of claim 6.

16. The phosphite ester produced by the process of claim 7.

17. The phosphite ester produced by the process of claim 8.

18. The phosphite ester produced by the process of claim 9.

19. The process of claim 1 wherein the glycol is pentaerythritol.

20. The phosphite ester produced by the process of claim 19.

* * * * *